United States Patent
Thomaschewski

(10) Patent No.: US 8,844,418 B2
(45) Date of Patent: Sep. 30, 2014

(54) DEVICE FOR GUIDING A SAW BLADE

(75) Inventor: Walter Thomaschewski, Filderstadt (DE)

(73) Assignee: C. & E. Fein GmbH (DE)

( * ) Notice: Subject to any disclaimer, the term of this patent is extended or adjusted under 35 U.S.C. 154(b) by 1352 days.

(21) Appl. No.: 11/849,875

(22) Filed: Sep. 4, 2007

(65) Prior Publication Data

US 2008/0066602 A1 Mar. 20, 2008

(30) Foreign Application Priority Data

Sep. 15, 2006 (DE) .................... 20 2006 014 895 U

(51) Int. Cl.
*B27B 11/02* (2006.01)

(52) U.S. Cl.
USPC .......................................................... 83/821

(58) Field of Classification Search
USPC ............................... 83/821, 441, 573; 606/79
See application file for complete search history.

(56) References Cited

U.S. PATENT DOCUMENTS

| | | | |
|---|---|---|---|
| 1,381,033 A | | 6/1921 | Thornton |
| 4,299,152 A | * | 11/1981 | Ambler ........................... 83/763 |
| 4,736,737 A | * | 4/1988 | Fargie et al. .................... 606/88 |
| 5,092,869 A | * | 3/1992 | Waldron ......................... 606/82 |
| 5,182,975 A | * | 2/1993 | Warner ........................... 83/745 |
| 5,454,816 A | * | 10/1995 | Ashby ............................. 606/88 |
| 5,693,056 A | * | 12/1997 | Carls et al. .................. 606/86 R |
| 5,911,723 A | * | 6/1999 | Ashby et al. .................... 606/88 |
| 5,916,221 A | * | 6/1999 | Hodorek et al. ................ 606/89 |
| 5,925,049 A | | 7/1999 | Gustilo et al. |
| 5,938,665 A | * | 8/1999 | Martin ............................. 606/88 |
| 6,272,964 B1 | * | 8/2001 | Heilshov ......................... 83/821 |
| 6,458,135 B1 | * | 10/2002 | Harwin et al. .................. 606/88 |
| 6,688,208 B2 | * | 2/2004 | Campbell et al. ............... 83/743 |
| 6,757,981 B2 | * | 7/2004 | Hampton ........................ 30/372 |
| 7,104,997 B2 | * | 9/2006 | Lionberger et al. ............. 606/88 |
| 7,240,596 B1 | * | 7/2007 | Campbell et al. ............... 83/743 |
| 7,621,919 B2 | * | 11/2009 | Williams et al. ................ 606/87 |
| 7,648,505 B2 | * | 1/2010 | Squires et al. .................. 606/79 |
| 2001/0041524 A1 | | 11/2001 | Steiger et al. |
| 2003/0171757 A1 | * | 9/2003 | Coon et al. ...................... 606/87 |

(Continued)

FOREIGN PATENT DOCUMENTS

| | | |
|---|---|---|
| EP | 0466659 | 1/1992 |
| EP | 0 881 023 | 12/1998 |
| FR | 2590159 | 5/1987 |

OTHER PUBLICATIONS

Magrab, Edward B. "Integrated Product and Process Design and Development" copyright CRC Press 1997. pp. 143 and 204.*

(Continued)

*Primary Examiner* — Sean Michalski
(74) *Attorney, Agent, or Firm* — St. Onge Steward Johnston & Reens LLC

(57) ABSTRACT

The invention describes a device for guiding a saw blade, in particular a saw blade that is driven in an oscillating way, having a base body through which a guide slot extends for guiding a saw blade, which guide slot opens into a first guide surface configured as contact surface for the workpiece, having a stop which is supported on the base body and which comprises a second guide surface configured for being brought into contact with the workpiece and arranged at an angle relative to the first guide surface, and having a handle as means for holding the base body.

18 Claims, 2 Drawing Sheets

(56) References Cited

U.S. PATENT DOCUMENTS

| | | | |
|---|---|---|---|
| 2003/0216741 A1* | 11/2003 | Sanford et al. | 606/87 |
| 2004/0260301 A1 | 12/2004 | Lionberger et al. | |
| 2005/0183559 A1* | 8/2005 | Rue | 83/574 |
| 2005/0228393 A1* | 10/2005 | Williams et al. | 606/87 |
| 2005/0240196 A1 | 10/2005 | Davis et al. | |
| 2006/0111725 A1 | 5/2006 | Biegun | |
| 2007/0198022 A1* | 8/2007 | Lang et al. | 606/88 |

OTHER PUBLICATIONS

Oberg, Erik; Jones, Franklin D.; Horton, Holbrook L.; Ryffel, Henry H. (2004). Machinery's Handbook (27th Edition) & Guide to Machinery's Handbook.. Industrial Press. p. 1512. Online version available at: http://www.knovel.com/web/portal/browse/display?__EXT_KNOVEL_DISPLAY_bookid=1074&VerticalID=0.*

EP Search Report, Dec. 21, 2007, 4 pages.

* cited by examiner

DEVICE FOR GUIDING A SAW BLADE

CROSS-REFERENCE TO RELATED APPLICATIONS

This application claims Convention priority of German utility model application DE 20 2006 014 895.7 filed on Sep. 15, 2006 the subject matter of which is fully incorporated by reference herewith

FIELD OF THE INVENTION

The present invention relates to a device for guiding a saw blade, in particular for a saw blade that is driven in an oscillating way.

BACKGROUND OF THE INVENTION

Oscillatingly driven cutting tools of the kind basically known from EP 0 881 023 A2 have been in use for some time for special sawing work.

The drive used for that purpose is an oscillating drive that sets a drive shaft in reciprocating oscillating motion about its longitudinal axis, at high frequency and with a small angle of swing. A saw blade is mounted on one end of the drive shaft. The saw blade may be circular, segment-shaped or triangular, but may also have a longitudinal shape, as known from the before-mentioned printed publication. Especially an oblong configuration of the saw blade, where a cutting edge is formed on an end opposite a mounting opening of the saw blade, is of particular interest for special sawing work, such an arrangement allowing slot-shaped openings to be easily produced in numerous relatively inaccessible areas. In this way, approximately rectangular slots can be produced in wood, gypsum, stone or other materials.

However, due to the oscillating drive it is difficult to correctly locate the tool on the workpiece for precisely positioning a cut.

SUMMARY OF THE INVENTION

It is a first object of the present invention to disclose a device that allows cuts to be realized as precisely as possible.

It is a second object of the present invention to disclose a device for setting blind cuts into a material using saw blades that are driven in an oscillating way.

It is a third object of the invention to disclose a holding device which can be used in combination with an oscillatingly driven tool for preparing flat cuts on various workpieces.

According to the invention, these and other objects are achieved by a device for guiding a saw blade, in particular a saw blade that is driven in an oscillating way, having a base body through which a guide slot extends for guiding a saw blade, which guide slot opens into a first guide surface intended as contact surface for the workpiece, having a stop which is supported on the base body and which comprises a second guide surface intended for being brought into contact with the workpiece and arranged at an angle relative to the first guide surface, and having a handle as means for holding the base body.

Thus the object of the invention is fully solved in this way.

Using the device according to the invention, the guide slot intended to guide a saw blade can be precisely located on a workpiece using at least two guide surfaces. The guide slot exactly defines the location of the saw blade as it penetrates into the workpiece through the slot. It is thereby possible to produce slots in workpieces precisely in predefined positions.

According to an advantageous further development of the invention, the stop is received on the base body in sliding arrangement.

It is possible in this way to make the spacing between the saw blade—which is guided by the guide slot—and the second guide surface adjustable so that the spacing of the slot to be produced and the workpiece surface is rendered adjustable.

Preferably, the second guide surface is arranged at a right angle relative to the first guide surface.

This allows especially easy handling because in this case the device can be applied to a rectangular outer edge of the workpiece by the two guide surfaces arranged one at a right angle to the other.

Generally, it would however also be possible to make the angle between the two guide surfaces adjustable in case working of non-rectangular workpieces is desired.

The base body and the handle are preferably designed as one integral plastic part, preferably as an injection-molded part.

In this way, especially simple and low-cost production is achieved.

According to a further embodiment of the invention, the guide slot is formed in a metallic insert in the base body.

One thereby prevents premature abrasion of the guide slot in case the latter consists of a plastic material. The metal insert may, for example, consist of aluminum or steel.

According to a further embodiment of the invention, the stop is configured as an angle that is slidably guided on a seat of the base body by a guide element.

In this way, a simple structure and an easy way of adjusting the spacing between the second guide surface and the guide slot is achieved.

According to an additional further improvement of that embodiment, the guide element is held on the seat and can be fixed in place by clamping elements.

It is thereby possible to adjust and fix a predefined spacing between a workpiece surface and the slot to be produced before a cutting operation is started.

The clamping element may for this purpose comprise screws that pass through the base body and engage threaded elements by means of which the guide element can be urged against the seat.

This provides an especially simple way of adjusting the stop.

According to a further embodiment of the invention, the stop is configured as a plastic part, preferably as an injection-molded part.

This provides a simple and low-cost way of producing the stop.

According to a further embodiment of the invention, a scale is provided in the base body for indicating the spacing between the slot and the second guide surface.

This feature facilitates the process of pre-adjusting the spacing between the second guide surface, formed by the stop, and the guide slot.

According to a further embodiment of the invention, the first guide surface on the base body is passed by at least one opening.

This makes it possible to fix and, thus, securely locate the base body on a workpiece using a screw before the sawing operation is started.

According to a further embodiment of the invention, the guide surface on the stop is passed by at least one opening.

It is possible in this case to fix the device on the workpiece using the stop, either alternatively or additionally, with the aid of a screw for example. The second guide surface on the stop may be provided for this purpose with one or more slots, for example.

It is understood that the features of the invention mentioned above and those yet to be explained below can be used not only in the respective combination indicated, but also in other combinations or in isolation, without leaving the scope of the invention.

BRIEF DESCRIPTION OF THE DRAWINGS

Further features and advantages of the invention will become apparent from the description that follows of a preferred embodiment of the invention, with reference to the drawing. In the drawings.

DETAILED DESCRIPTION OF THE INVENTION

Figure 1:
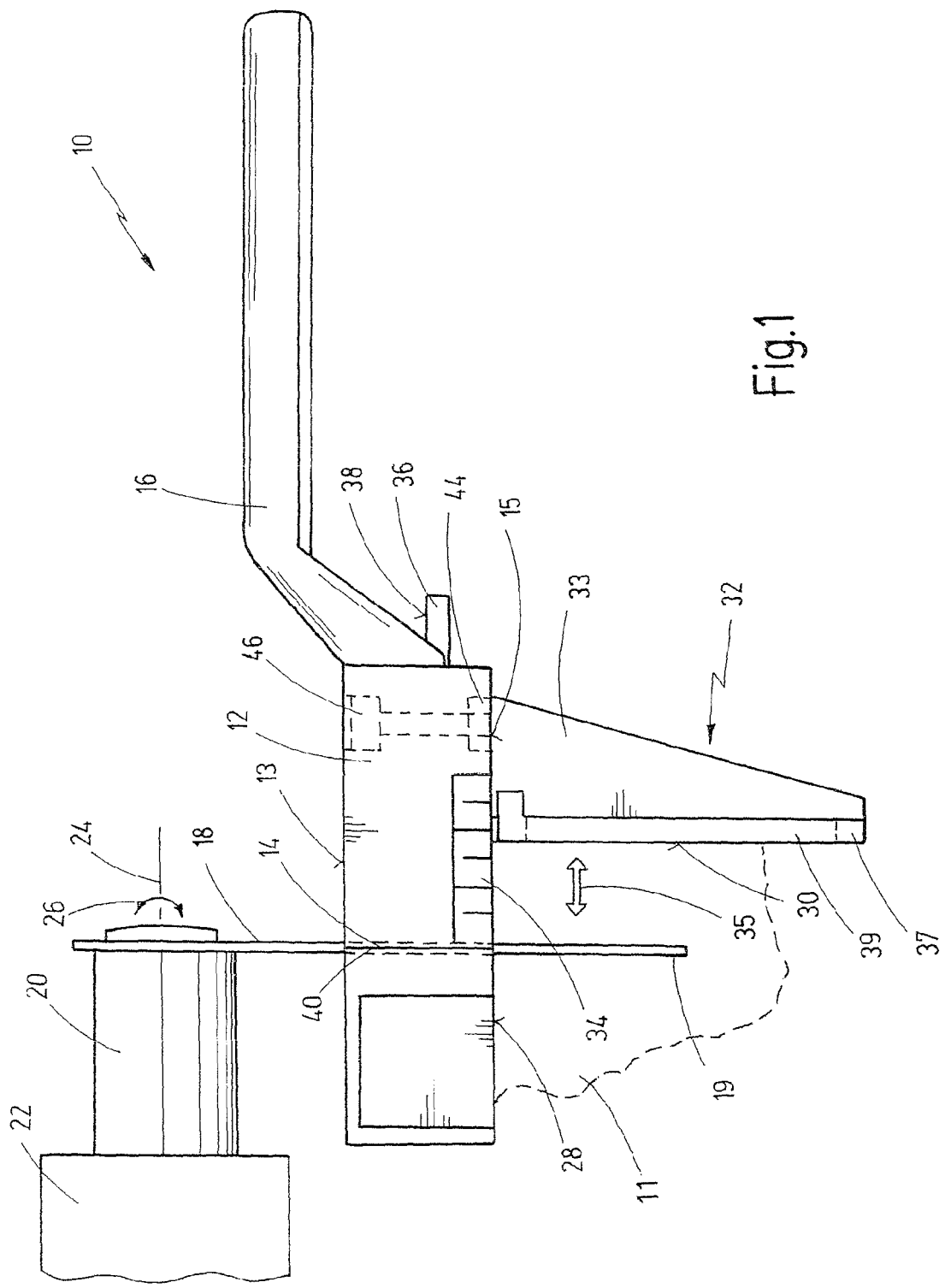
FIG. 1 shows a side view of a device according to the invention, with an oscillating drive and a saw blade indicated additionally, the saw blade being guided through the guide slot of the device in which position it can be used for producing a slot-shaped cut in the workpiece.
Figure 2:
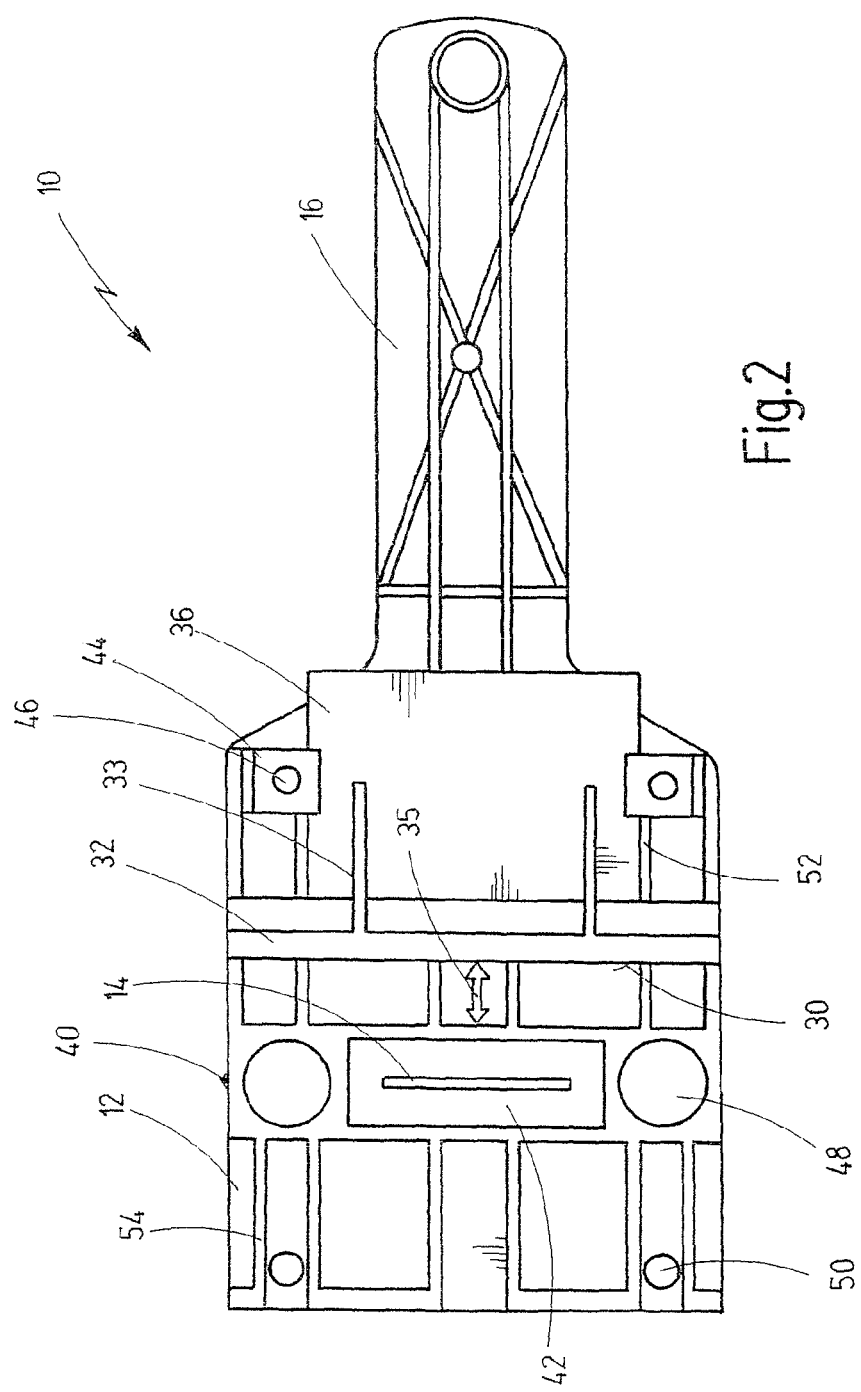
FIG. 2 shows a bottom view of the device illustrated in FIG. 1.

In FIGS. 1 and 2 a device according to the invention is illustrated and generally indicated by reference numeral 10.

As can be seen in FIG. 2, the device 10 has an approximately cuboid base body 12 which instead of being configured as a solid body consists of a hollow profile structure. The resulting structure helps save both weight and material.

The base body can be held by a handle 16 mounted laterally on the body in angled fashion. The base body 12 comprises a first surface 13 on its upside and a second surface 15 at its bottom. A guide slot 14 of rectangular shape, serving to guide the tool 18 passed through the slot, extends between the first surface and the second surface.

In the illustrated case, the tool 18 consists of an oblong saw blade with a cutting edge 19 at its lower end, which is mounted on the drive shaft 20 of an oscillating drive 22 by its end opposite the cutting edge.

The oscillating drive 22 sets the drive shaft 20 in reciprocating oscillating movement about the longitudinal axis 24 of the drive shaft, as indicated by double arrow 26. As a rule, the drive operates at a high frequency of between 5,000 and 30,000 oscillations per minute, and with a small angle of swing of between 0.5 and 7 degrees.

Such a saw blade 18, set to oscillate in this way, can be used to produce slot-shaped cuts in numerous workpieces.

The device according to the invention serves in this case to precisely locate the cut and to ensure rectangular penetration of the saw blade into the workpiece 11 (schematically indicated by a dashed line in FIG. 1).

The second lower surface 15 of the base body 12 is configured as a first guide surface 28 that serves to guide the device along a workpiece surface.

Further, the base body 12 carries a rectangular stop 32 with a stop plate 37 projecting at a right angle from the first guide surface 28. The surface of the stop plate 37 forms a second guide surface 30.

As the stop 32 can be adjusted in parallel to the first guide surface 28 (compare arrow 35), as will be explained in more detail below with reference to FIG. 2, it is possible to adjust the spacing between the second guide surface 30 and the guide slot 14.

In order to facilitate such adjustment, a mark 40, indicating the middle of the guide slot 14, is provided on both sides of the base body 12, with a scale 34 extending from that mark.

The stop 32 is stiffened by two stiffening ribs 33 that extend from the stop plate 37 to a plate 36 arranged at a right angle relative to the stop plate 37. The plate 36 serves as guide element as guidance along a seat 52 (FIG. 2). Accordingly, the stop 32 can be adjusted along the seat by displacing the plate-shaped guide element 36, as indicated by arrow 35.

Once the position of the stop has been adjusted, it can be fixed in that position by threaded coupling pieces 44 in the form of small plates that are received on the bottom of the base body and that partly cover the guide element 36 laterally. The threaded coupling pieces 44 are held by screws 46 that are screwed into the surface 13 on the upside of the base body 12 and through the latter and that engage in the threaded coupling pieces 44. It is thereby possible to release the stop 32 in a desired position on the base body by untightening the screws 46, and to fix the stop 32 by tightening the screws 46 upon completion of the adjustment. This permits the spacing between the second guide surface 30 and the guide slot 14 to be preadjusted before a cut is made.

The base body 12 is passed by a plurality of openings 48, 50 that may serve for fixing the base body 12 on the workpiece, prior to making a cut, or that alternatively may be used as drilling jig when bores are to be produced. If the openings are to be used for the production of bores, then preferably metal inserts may be placed in the openings in order to prevent varying bore diameters as well as premature wear.

The base body 12 and the handle 16 may be formed as one integral injection-molded plastic part with a continuous surface on the side 13, and with a configuration as a hollow profile the bottom 15 of which is merely defined by a series of webs 54 that extend in downward direction thereby defining the first guide surface 28. The guide slot 14 is formed in an insert 42 made from a metal, preferably from steel.

The stop 32 may be configured as an injection-molded plastic part as well.

The stop plate 37 may be additionally passed by one or more holes 39, for example in the form of three slots that extend in the stop plate 37 from the top to the bottom, in parallel to the lateral outer surfaces.

The slots on the one hand serve to save weight and, on the other hand, may be used for temporarily fixing the device 10 on the workpiece surface before a cut is made, for example by tightening of a screw.

What is claimed is:

1. A device for guiding a saw blade oscillatingly driven by a hand-held oscillatory drive manually fed relative to said device, said device comprising:
    a base body having a guide slot that extends through the base body, the base body guiding the oscillatingly driven saw blade;
    the guide slot having a first guide surface, the first guide surface contacting a workpiece at a first surface thereof;
    a seat provided on said base body;
    an angled stop, the angled stop including:
        a guide element, the guide element slidingly received on said seat, and
        a second guide surface slidingly contacting the workpiece at a second surface thereof, said second guide surface arranged at an angle relative to said first guide surface to form a predefined spacing between said guide slot and the first surface of the workpiece, the predefined spacing being adjustable;

a handle protruding outwardly from said base body, the handle holding the device independently of said oscillatory drive; and fasteners for clamping said guide element against said seat and for securing said guide element thereon, said fasteners having screws that pass through said base body and engage threaded pieces provided on said base body for urging said guide element against said seat.

2. The device of claim 1, wherein said second guide surface is arranged at a right angle relative to said first guide surface.

3. The device of claim 1, wherein said base body and said handle are configured as one integral injection-molded plastic part.

4. The device of claim 3, wherein said base body further comprises a metallic insert wherein said guide slot is formed.

5. The device of claim 1, wherein said stop is configured as an injection-molded plastic part.

6. The device of claim 1, further comprising a scale provided on said base body for indicating a distance between said guide slot and said second guide surface.

7. The device of claim 1, wherein said first guide surface of said base body comprises at least one opening passing through said base body.

8. The device of claim 1, wherein said second guide surface of said angled stop comprises at least one opening passing therethrough.

9. A system for making cuts into a workpiece, said system comprising:
   a hand-held oscillatory drive for oscillatingly driving a saw blade; and
   a device for guiding a saw blade, said device including:
      a base body having a guide slot for guiding the saw blade that extends through the base body;
      said guide slot having a first guide surface, the first guide surface slidingly contacting a workpiece at a first surface thereof;
      a stop, the stop supported on said base body, the stop including a second guide surface slidingly contacting the workpiece at a second surface thereof, said second guide surface arranged at an angle relative to said first guide surface to form a predefined spacing between said guide slot and the first surface of the workpiece, the predefined spacing being adjustable;
      fasteners for clamping said guide element against said seat and for securing said guide element thereon, said fasteners having screws that pass through said base body and engage threaded pieces provided on said base body for urging said guide element against said seat; and
      a handle protruding outwardly from said base body, said handle holding the device independently of said oscillatory drive;
   wherein said oscillatory drive is configured for being manually fed relative to said device.

10. The device of claim 9, wherein said base body comprises a seat which is slidably engaged by a guide element provided on said stop.

11. The device of claim 10, wherein said stop is configured as an angled stop.

12. The device of claim 9, wherein said second guide surface is arranged at a right angle relative to said first guide surface.

13. The device of claim 9, wherein said base body further comprises a metallic insert wherein said guide slot is formed.

14. The device of claim 9, wherein said base body and said handle are configured as one integral plastic part.

15. The device of claim 14, wherein said base body further comprises a metallic insert wherein said guide slot is formed.

16. A system for making cuts into a workpiece, said system comprising:
   a hand-held oscillatory drive for oscillatingly driving a cutting tool;
   a device for guiding the cutting tool, said device including:
      a base body having a guide slot for guiding the cutting tool that extends through the base body;
      said guide slot having a first guide surface slidingly contacting a workpiece at a first surface thereof;
      a seat provided on said base body;
      an angled stop including:
         a guide element slidingly received on said seat,
         a second guide surface slidingly contacting the workpiece at a second surface thereof and being arranged at an angle relative to said first guide surface to form a predefined spacing between said guide slot and the first surface of the workpiece, the predefined spacing being adjustable;
      fasteners for clamping said guide element against said seat and for securing said guide element thereon, said fasteners having screws that pass through said base body and engage threaded pieces provided on said base body for urging said guide element against said seat; and
      a handle protruding outwardly from said base body and holding the device independently of said oscillatory drive;
   wherein said oscillatory drive is configured for being manually fed relative to said device.

17. The system of claim 16, further comprising a cutting tool that is configured as a saw blade having a longitudinal shape, said saw blade comprising:
   a lower end comprising a cutting edge; and
   an opposite end mounted on a drive shaft of said oscillatory drive;
   wherein said opposite end is arranged opposite said lower end and wherein said saw blade is configured for attachment to said oscillating drive.

18. The system of claim 16, wherein said base body and said handle are configured as one integral injection-molded plastic part, and wherein said base body further comprises a metallic insert where said guide slot is formed.

* * * * *